United States Patent
O'Heeron et al.

(10) Patent No.: US 11,975,030 B2
(45) Date of Patent: May 7, 2024

(54) TREATMENT OF CHRONIC OBSTRUCTIVE PULMONARY DISEASE AND LUNG DEGENERATION USING ACTIVATED FIBROBLASTS AND EXOSOME DERIVATIVES THEREOF

(71) Applicant: Figene, LLC, Houston, TX (US)

(72) Inventors: Pete O'Heeron, Houston, TX (US); Thomas Ichim, San Diego, CA (US)

(73) Assignee: Figene, LLC, Houston, TX (US)

( * ) Notice: Subject to any disclaimer, the term of this patent is extended or adjusted under 35 U.S.C. 154(b) by 557 days.

(21) Appl. No.: 16/822,811

(22) Filed: Mar. 18, 2020

(65) Prior Publication Data

US 2020/0297774 A1    Sep. 24, 2020

Related U.S. Application Data

(60) Provisional application No. 62/820,763, filed on Mar. 19, 2019.

(51) Int. Cl.
*A61K 35/33* (2015.01)
*A61K 31/522* (2006.01)
*A61K 31/56* (2006.01)
*A61K 45/06* (2006.01)

(52) U.S. Cl.
CPC .......... *A61K 35/33* (2013.01); *A61K 31/522* (2013.01); *A61K 31/56* (2013.01); *A61K 45/06* (2013.01)

(58) Field of Classification Search
None
See application file for complete search history.

(56) References Cited

U.S. PATENT DOCUMENTS

2012/0308585 A1 * 12/2012 Lombardo .............. A61P 37/02 435/325
2014/0031252 A1    1/2014 Rennard et al.
2018/0333438 A1   11/2018 Stewart

FOREIGN PATENT DOCUMENTS

| JP | 2017/513944 | 6/2017 |
| JP | 2018/502556 | 2/2018 |
| JP | 2018/118984 | 8/2018 |
| WO | 2001/021184 A1 | 3/2001 |
| WO | WO 2010/151640 | 12/2010 |
| WO | WO 2013/167582 | 11/2013 |

OTHER PUBLICATIONS

Salimian, Jafar. Chronic Obstructive pulmonary disease: MicroRNas and exosomes as new diagnostic and therapeutic biomarkers. J Res Med Sci 2018 23:27, 11-2.*
Falk, Jeremy A. Inhaled and Systemic Corticosteroids in Chronic Obstructive Pulmonary Disease. Proc Am Thorac Soc, 5, 506-512, 2008.*
Extended European Search Report issued in European Patent Application No. 20773901.2, dated Aug. 10, 2022.
GE et al., "Basic fibroblast growth factoe activateds β-catenin/ RhoA signaling in pulmonary fibroblasts with chronic obstructive pulmonary disease in rats," 423(1-2):165-174, 2016.
Lacy et al., "Activated Human Lung Fibroblasts Prodice Extracellular Vesicles with Antifibrotic Prostaglandins," 60(3):369-278, 2019.
Müller et al., "Lung fibroblasts from patients with emphyseman show markers of senescence in vitro," 7(1):32, 10 pages, 2006.
Zandvoort et al., "Smad gene expression in pulmonary fibroblasts: indications for defective ECM repair in CORD," 9(1):83, 10 pages, 2008.
Sayed et al. "Transdifferentlation of Human Fibroblasts to Endothelial Cells: Role of Innate Immunity" Circulation, Jan. 20, 2015; 131(3): pp. 300-309; abstract; p. 6.
Kardia et al. "Aerosol-Based Delivery of Fibroblast Cells for Treatment of Lung Diseases" Journal of Aerosol Medicine and Pulmonary Drug Delivery, 2014, vol. 27, No. 1, pp. 30-34.
Office Communication issued in Japanese Patent Application No. 2021-556792, dated Dec. 11, 2023, with English translation.

* cited by examiner

*Primary Examiner* — Samantha L Shterengarts
(74) *Attorney, Agent, or Firm* — Norton Rose Fulbright US LLP

(57) ABSTRACT

Embodiments of the disclosure include methods and compositions for treatment of lung disease, including at least chronic obstructive pulmonary disease (COPD). In particular cases, fibroblasts (including activated fibroblasts) and/or exosomes thereof are provided to an individual for the treatment of COPD. In particular cases the fibroblasts are activated and/or express one or more particular markers.

7 Claims, No Drawings

TREATMENT OF CHRONIC OBSTRUCTIVE PULMONARY DISEASE AND LUNG DEGENERATION USING ACTIVATED FIBROBLASTS AND EXOSOME DERIVATIVES THEREOF

This application claims priority to U.S. Provisional Patent Application Ser. No. 62/820,763, filed Mar. 19, 2019, which is incorporated by reference herein in its entirety.

TECHNICAL FIELD

Embodiments of the disclosure include at least the fields of cell biology, molecular biology, cell therapy, and medicine.

BACKGROUND

Chronic Obstructive Pulmonary Disease (COPD), an umbrella term covering chronic bronchitis and emphysema, is the fourth largest cause of death in the United States and is projected to be the third by 2020 [1]. COPD is associated with an exaggerated chronic inflammatory response that is responsible for the airway abnormalities, such as constriction and architectural distortion of the lung parenchyma. Patients generally undergo a progression of declining lung function, characterized by intensification of cough, shortness of breath, and sputum production. Extrapulmonary manifestations of COPD include osteoporosis, cardiovascular disease, skeletal muscle abnormalities, and depression [2]. Chronic obstructive pulmonary disease (COPD) is a significant cause of morbidity and mortality worldwide. In contrast to other chronic diseases, COPD is increasing in prevalence. The costs to society for treating COPD are high, accounting for approximately 3.4% of the total health care budget of the European Union. In the United States, the direct and indirect costs of COPD are estimated to be more than 30 billion.

It is known that 30% of patients with COPD have elevated levels of eosinophils in the airway as measured by sputum induction or bronchoalveolar lavage. In COPD, the response to oral and inhaled corticosteroids (ICS) is related to the intensity of the airway eosinophilic inflammation, and a sputum eosinophilia count of greater than 3% has been demonstrated to be a good predictor of response to steroids in COPD. A strategy in which increasing therapy with corticosteroids was used to control sputum eosinophilia greater than 3% in COPD resulted in a reduction in the frequency of severe COPD exacerbations requiring admission to a hospital when patients were stepped up to oral corticosteroid therapy. Standard therapy for acute exacerbations of COPD (AECOPD) includes treatment of inflammation with systemic corticosteroids, which are associated with a reduction in length of hospital stay and hastened recovery. Corticosteroids are responsible for early apoptosis of eosinophils and generally result in a reduction in eosinophilia. Unfortunately, long-term therapy with corticosteroids is associated with significant side effects, such as suppression of the hypothalamic-pituitary-adrenal axis and osteoporosis, and corticosteroids do not avert exacerbations in all eosinophilic COPD patients.

COPD patients with increased sputum eosinophil counts have been shown to have significant improvements in forced expiratory volume in 1 second ($FEV_1$) and quality of life-scores that were associated with decreased sputum eosinophil counts and eosinophil cationic protein (ECP) levels. Thus, therapies specifically targeted at eosinophils in COPD may have beneficial effects.

Current treatments for COPD are primarily palliative and are based on severity of disease. According to the Global Strategy for the Diagnosis, Management, and Prevention of COPD (GOLD) guidelines, the following treatments are recommended: Stage I, which is characterized by mild obstruction, the aim is to reduce risk factors associated with exacerbations, for example by providing flu vaccine and use of short-acting bronchodilator as needed. Stage II patients are classified as moderate obstruction, where risk factors are to be reduced by vaccination, and the use of long-acting bronchodilators, as well as cardiopulmonary rehabilitation is advised in addition to short-acting bronchodilators. Patients with Stage III disease are considered to suffer from severe obstruction, in which inhaled glucocorticoids are added to the regime of Stage II. In Stage IV, which is considered very severe obstruction or moderate obstruction with evidence of chronic respiratory failure, long-term oxygen therapy is added, as well as consideration of surgical options such as lung volume reduction surgery and lung transplantation [3].

The present disclosure provides methods and compositions related to novel and effective treatments for lung diseases including COPD.

BRIEF SUMMARY

Embodiments of the disclosure include methods and compositions for treating and preventing lung disease, including lung degenerative diseases in which lung tissue of any kind is degenerated. In specific embodiments the disease is COPD, asthma, partial or complete lung collapse, lung infection, pulmonary edema, pulmonary embolus, bronchitis, emphysema, or a combination thereof. In particular embodiments, the individual is previously diagnosed as having lung disease or lung degeneration of any kind, although in some cases the individual has not been previously diagnosed. An individual may utilize the methods if they are at risk for having lung disease, such as being or having been a smoker and/or having been in or being in an environment hazardous to lung health, including at home and/or the workplace. Examples include exposure to asbestos, beryllium, cotton, flax, hemp silica, gas, chemicals, coal, graphite, and so forth.

In particular embodiments, the individual is experiencing and/or has experienced one or more acute respiratory symptoms that may be referred to as a COPD exacerbation, which includes shortness of breath, especially during physical activities; wheezing; chest tightness; having to clear their throat first thing in the morning, such as because of excess mucus in their lungs; and/or a chronic cough that may produce mucus (sputum) that may be clear, white, yellow or greenish.

Methods and compositions include administration of fibroblasts (that may be activated) and/or exosomes thereof. The fibroblasts may comprise one or more certain markers, such as CD34 and/or CD73. The fibroblasts may be activated in any manner, including by exposure to activated protein C and/or one or more toll like receptor agonists.

Embodiments of the disclosure include methods of treating or preventing lung disease and/or degeneration in an individual, comprising the step of administering an effective amount of fibroblasts and/or exosomes thereof to an individual with lung disease or at risk for lung disease. In specific embodiments, the fibroblasts are activated and/or express one or more specific markers. The fibroblasts may be activated by exposure to at least one toll like receptor agonist and/or by exposure to Activated Protein C. The toll like receptor may be TLR-1, TLR-2, TLF-3, TLR-4, TLR-5, TLR-6, TLR-7, TLR-8, or TLR-9. In particular embodiments, the fibroblasts express one or more markers selected from the group consisting of CD31, CD73, and a combination thereof. In particular embodiments, the lung disease is chronic obstructive pulmonary disease. The individual is or was a smoker, in specific cases. In certain embodiments, the individual is provided an effective amount of another therapy for the lung disease, such as therapy comprising short- and long-acting beta2-agonists, anticholinergics, one or more corticosteroids, one or more phosphodiesterase-4 inhibitors, theophylline, supplemental oxygen therapy, and/or surgery.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

DETAILED DESCRIPTION

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

I. Examples of Definitions

The term "administered" or "administering", as used herein, refers to any method of providing a composition to an individual such that the composition has its intended effect on the patient. For example, one method of administering is by an indirect mechanism using a medical device such as, but not limited to a catheter, applicator gun, syringe etc. A second exemplary method of administering is by a direct mechanism such as, local tissue administration, oral ingestion, transdermal patch, topical, inhalation, suppository etc.

The term "allogeneic," as used herein, refers to cells of the same species that differ genetically from cells of a host.

The term "autologous," as used herein, refers to cells derived from the same subject. The term "engraft" as used herein refers to the process of stem cell incorporation into a tissue of interest in vivo through contact with existing cells of the tissue.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%. With respect to biological systems or processes, the term can mean within an order of magnitude, preferably within 5-fold, and more preferably within 2-fold, of a value. Unless otherwise stated, the term 'about' means within an acceptable error range for the particular value.

As used herein, the term "activated fibroblasts" refers to fibroblasts treated with one or more stimuli capable of inducing one or more alterations in the cell: metabolic, immunological, growth factor-secreting, surface marker expression, and/or production of microvesicles.

"Cell culture" is an artificial in vitro system containing viable cells, whether quiescent, senescent or (actively) dividing. In a cell culture, cells are grown and maintained at an appropriate temperature, typically a temperature of 37° C. and under an atmosphere typically containing oxygen and CO2. Culture conditions may vary widely for each cell type though, and variation of conditions for a particular cell type can result in different phenotypes being expressed. The most commonly varied factor in culture systems is the growth medium. Growth media can vary in concentration of nutrients, growth factors, and the presence of other components. The growth factors used to supplement media are often derived from animal blood, such as calf serum.

As used herein, the term "conditioned medium of fibroblast regenerative cells" refers to a liquid media which has been in contact with cells, wherein said cells produce factors which enter the media, thus bestowing upon the media therapeutic activity.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term "subject" or "individual", as used herein, refers to a human or animal that may or may not be housed in a medical facility and may be treated as an outpatient of a medical facility. The individual may be receiving one or more medical compositions via the internet. An individual may comprise any age of a human or non-human animal and therefore includes both adult and juveniles (i.e., children) and infants. It is not intended that the term "individual" connote a need for medical treatment, therefore, an individual may voluntarily or involuntarily be part of experimentation whether clinical or in support of basic science studies. The term "subject" or "individual" refers to any organism or animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals.

As used herein, the term "therapeutically effective amount" is synonymous with "effective amount", "therapeutically effective dose", and/or "effective dose" and refers to the amount of compound that will elicit the biological, cosmetic or clinical response being sought by the practitioner in an individual in need thereof. As one example, an effective amount is the amount sufficient to reduce immunogenicity of a group of cells. As a non-limiting example, an effective amount is an amount sufficient to promote formation of a blood supply sufficient to support the transplanted tissue. As another non-limiting example, an effective amount is an amount sufficient to promote formation of new blood vessels and associated vasculature (angiogenesis) and/or an amount sufficient to promote repair or remodeling of existing blood vessels and associated vasculature. The appropriate effective amount to be administered for a particular application of the disclosed methods can be determined by those skilled in the art, using the guidance provided herein. For example, an effective amount can be extrapolated from in vitro and in vivo assays as described in the present specification. One skilled in the art will recognize that the condition of the individual can be monitored throughout the course of therapy and that the effective amount of a compound or composition disclosed herein that is administered can be adjusted accordingly.

"Treatment," "treat," or "treating" means a method of reducing the effects of a disease or condition. Treatment can also refer to a method of reducing the disease or condition itself rather than just the symptoms. The treatment can be any reduction from pre-treatment levels and can be but is not limited to the complete ablation of the disease, condition, or the symptoms of the disease or condition. Therefore, in the disclosed methods, treatment" can refer to a 10%, 20%, 30%, 40%, 50%, 60%, 70%, 80%, 90%, or 100% reduction in the severity of an established disease or the disease progression, including reduction in the severity of at least one symptom of the disease. For example, a disclosed method for reducing the immunogenicity of cells is considered to be a treatment if there is a detectable reduction in the immunogenicity of cells when compared to pre-treatment levels in the same subject or control subjects. Thus, the reduction can be a 10, 20, 30, 40, 50, 60, 70, 80, 90, 100%, or any amount of reduction in between as compared to native or control levels. It is understood and herein contemplated that "treatment" does not necessarily refer to a cure of the disease or condition, but an improvement in the outlook of a disease or condition. In specific embodiments, treatment refers to the lessening in severity or extent of at least one symptom and may alternatively or in addition refer to a delay in the onset of at least one symptom.

II. Methods of Manufacture and Use

The present disclosure concerns methods and compositions related to prevention and treatment of lung disease of any kind, including lung degenerative diseases (for example, wherein the function or structure of the affected tissues or organs changes for the worse over time), such as at least chronic obstructive pulmonary disease (COPD). Symptoms of COPD include shortness of breath, after even mild exercise such as walking up a flight of stairs; wheezing, which is a type of higher pitched noisy breathing, especially during exhalations; chest tightness; chronic cough, with or without mucus; a need to clear mucus from the lungs every day; frequent colds, flu, or other respiratory infections; lack of energy; fatigue; swelling of the feet, ankles, or legs; and/or weight loss, for example.

In particular embodiments, the methods and compositions concern using fibroblasts alone, and/or fibroblasts that are activated, for the treatment of lung disease. In at least specific cases, the fibroblasts (activated or not) are utilized in order to endow enhanced regenerative activity of any type of lung tissue. The individual may be a smoker or have smoked in the past; may have been exposed to lung irritants in the workplace; may have been exposed to a lot of secondhand smoke; may have a family or personal history of COPD; and/or may have asthma or other respiratory conditions. The individual may have a genetic disorder involving a deficiency of the protein alpha-1-antitrypsin, in some cases.

In some embodiments, methods of the current disclosure comprise administering fibroblast regenerative cells (regenerative to lung tissue), a population or plurality or culture of fibroblast regenerative cells, progeny of fibroblast regenerative cells or conditioned medium of fibroblast regenerative cells to treat a subject having or at risk of having lung disease including COPD. Fibroblast regenerative cells can be administered or delivered to a subject by any route suitable for the treatment method or protocol. Specific non-limiting examples of administration and delivery routes include parenteral, e.g., intravenous, intramuscular, intrathecal (intra-spinal), intrarterial, intradermal, subcutaneous, intra-pleural, transdermal (topical), transmucosal, intra-cranial, intra-ocular, mucosal, implantation and transplantation.

In one embodiment, fibroblasts for lung disease treatment, including COPD treatment, are activated, and the activation of the fibroblasts may or may not be performed through stimulation with a particular compound(s) and/or condition. In specific cases, the compound is a toll like receptor agonist. In specific cases, the stimulation with a toll like receptor agonist occurs at a concentration and for a duration sufficient to induce a >50% increase in keratinocyte growth factor expression from the fibroblasts, as an example in a typical tissue culture situation where fibroblasts are grown at 75% confluence in DMEM media with 10% fetal calf serum and exposed to a toll like receptor agonist for 24 hours. In one embodiment, the disclosure provides the use of fibroblasts as a means of producing exosomes, wherein the exosomes possess therapeutic properties capable of providing treatment and/or prevention of lung disease. For example, the exosomes from the fibroblasts (activated or not) may reduce inflammation, fibrosis and degeneration associated with COPD, as well as resulting in stimulation of regenerative activity. In some cases, fibroblasts are activated by a treatment with a particular compound, such as Activated Protein C.

Embodiments of the disclosure include methods of treating a lung degenerative disease comprising administration of therapeutic cells, wherein the therapeutic cells are generated by the steps of: a) obtaining fibroblasts; b) culturing the fibroblasts in a liquid media capable of allowing for proliferation of the fibroblasts; c) extracting from the culture cells expressing the markers CD31 and/or CD73; and d) priming the CD31 and/or CD73-positive cells with one or more agents capable of augmenting production of lung regenerative properties of the CD31 and/or CD73-positive cells. In specific embodiments, the lung regenerative properties are selected from the group consisting of: a) inhibiting inflammation; b) enhancing renewal of pulmonary progenitor cells; c) inhibiting pulmonary fibrosis (for example, by augmentation of matrix metalloprotease (of any kind) activity; d) preventing apoptosis of pulmonary cells (for example, by production of IGF-1 and/or VEGF in the fibroblasts (endogenously produced or through expression of an exogenously provided polynucleotide); and e) a combination thereof. The inflammatory cytokines (for example, from diseased lung) may be associated with increasing permeability of blood vessels. The inflammatory cytokines may be associated with induction of hypotension. The inflammatory cytokines may be associated with induction of vascular leakage. The inflammatory cytokines may be associated with an increase in pro-thrombotic molecules on the vasculature.

In specific embodiments, an example of a lung regenerative cytokine from the fibroblasts is keratinocyte growth factor, ciliary neurotrophic growth factor, or both.

In some embodiments, fibroblasts utilized for prevention or treatment of lung disease are activated. They may be activated by any particular means, but in specific embodiments they are activated by exposure to one or more compounds, such as one or more toll like receptor agonists. In specific cases, the toll like receptor is TLR-1, although in other cases the toll like receptor is TLR2, TLR3, TLR4, TLR5, TLR6, TLR7, TLR8, TLR9, TLR10, TLR11, TLR12, or TLR13, In certain embodiments, the agonist of a toll like receptor is an agonist of TLR-1, such as Pam3CSK4. In some cases, the toll like receptor is TLR-2, and the agonist may be HKLM. In certain cases, the toll like receptor is TLR-3, and the agonist of TLR-3 may be Poly:IC. In certain cases, the toll like receptor is TLR-4, and the agonist of TLR-4 is LPS, Buprenorphine, Carbamazepine, Fentanyl, Levorphanol, Methadone, Cocaine, Morphine, Oxcarbazepine, Oxycodone, Pethidine, Glucuronoxylomannan from Cryptococcus, Morphine-3-glucuronide, lipoteichoic acid, β-defensin 2, small molecular weight hyaluronic acid, fibronectin EDA, snapin, tenascin C, or a combination thereof. In certain cases the toll like receptor is TLR-5, and the agonist is flagellin. In some cases, the toll like receptor is TLR-6, and the agonist is FSL-1. In some cases, the toll like receptor is TLR-7, and the agonist is imiquimod. In certain cases, the toll like receptor of TLR-8, and the agonist is ssRNA40/LyoVec. In some cases, the toll like receptor is TLR-9, and the agonist is a CpG oligonucleotide, ODN2006, Agatolimod, or a combination thereof.

In particular embodiments, the disclosure concerns administration of fibroblasts, including placental fibroblasts, for example, for treatment of COPD. In some cases, administration of the fibroblasts is performed using cells that have been activated prior to administration. The process of activating fibroblasts may be performed in order to augment regenerative, and/or anti-inflammatory, and/or migratory, and/or anti-apoptotic, and/or anti-fibrotic activities of the fibroblasts.

The disclosure concerns use of fibroblasts, in a particular embodiment, including fibroblasts possessing expression of CD34 and/or CD73, for treatment of a lung disease such as COPD. In one particular embodiment, COPD is caused in part by cytokine upregulation, as well as subacute production of disseminated intravascular coagulation response causing degeneration of the alveoli. In one specific embodiment, fibroblasts are primed with one or more inflammatory or proinflammatory signals in order to elicit a corresponding anti-inflammatory and pro-regenerative profile (when fibroblasts are treated with inflammatory agents they respond by suppressing inflammation) (Inflammatory: TNF, IL1-1, IL-6, IL-18; Anti-inflammatory IL-10).

In one embodiment of the disclosure is the novel finding that prestimulation of fibroblasts with activated protein C (APC) is useful as a means of increasing anti-inflammatory potency of fibroblasts. The anti-inflammatory potency may be utilized as a means of protecting individuals from lung disease, such as COPD, and inducing regeneration of at least some pulmonary tissue.

The disclosure regards means of selecting fibroblasts for enhanced efficacy based on expression of one or more certain markers and/or lack of expression of one or more certain markers. In specific embodiments, the fibroblasts (whether or not they are activated) express CD73 and/or CD34 and may also lack of expression of one or more certain proteins.

The use of fibroblasts for treatment of lung disease or degeneration may be based, in one embodiment of the disclosure, on the reduction of one or more pathological immunological parameters associated with the lung disease or degeneration, such as COPD. One of skill in the art is referred to publications supporting immunological mediated pathology in COPD [4], including specific demonstration that the destruction of alveolar tissue is associated with T cell reactivity [5, 6], pathological pulmonary macrophage activation [7], and auto-antibody production [8]. In one embodiment, fibroblasts are utilized to treat COPD. In specific embodiments, the fibroblasts are employed for participating indirectly or directly with immune regulation including suppressing autoreactive T cells [9, 10], inhibiting macrophage activation [11], and also downregulating autoantibody responses [12].

In some embodiments, the treatment of lung disease or degeneration such as COPD is performed prophylactically by administration of fibroblasts, including activated fibroblasts. Initiation of COPD is believed to occur in many cases as result of one or more noxious agents, particularly, but not exclusively in cigarette smoke. One established mechanism of initial alveolar injury involves smoke-induced activation of inducible nitric oxide synthase (iNOS), which in turn produces cytotoxic free radicals such as peroxynitrite (ONOO−), which cause in mice a condition resembling emphysema. Interestingly, mice lacking iNOS, or treated with a chemical inhibitor, had some degree of protection from cigarette smoke-induced pathology [15]. Thus, in one embodiment, fibroblasts and/or derivatives thereof are administered in order to reduce activation of iNOS and/or reduce cytotoxic free radical-induced damage, including at least peroxynitrite-induced damage.

In some embodiments, the fibroblasts inhibit neutrophil activation in an individual with lung disease or at a risk for lung disease over the general population. Studies using human neutrophils have shown that nicotine itself stimulates neutrophils to produce the inflammatory cytokine interleukin-8, in an iNOS-dependent manner [16]. Accordingly, in one embodiment the disclosure concerns the use of fibroblasts for reduction of neurophil activation. Indeed, the same study demonstrated that smokers possessed higher systemic levels of interleukin-8 as compared to non-smokers. This is correlated in patients with COPD that have higher inflammatory markers compared to controls, including TNF-alpha and IL-8 [17]. Therefore, in specific embodiments, the fibroblasts directly or indirectly reduce levels of certain inflammatory markers including TNF-alpha and/or IL-8, for example.

Another mechanism associated with COPD initiation is the generation of collagen degradation products, such as the tripeptide chemoattractant N-acetyl Pro-Gly-Pro (PGP), which potently elicits neutrophil retention and activation. PGP is found in significantly higher concentrations in lavage samples of COPD patients as compared to controls, and also has been demonstrated to induce a COPD-like condition when administered into experimental animals [18]. Matrix metalloprotease (MMP)-9 has been demonstrated to be involved in the generation of PGP from collagen, and treatment of neutrophils with this agent stimulates their activation of MMP-9, thus suggesting an autostimulatory loop [19]. In particular embodiments, fibroblasts are provided to an individual with lung disease or at risk thereof to reduce directly or indirectly the generation of collagen degradation products of any kind. The collagen degradation may be reduced or delayed in onset in specific embodiments. Reduction in the level of PGP may occur upon administration of fibroblasts.

Inflammatory conditions stimulated by free radical stress and extracellular matrix degradation products stimulate various receptors within the lung to cause damage, and/or inhibit regeneration. For example, RTP801 is a protein that is inducible by HIF-1alpha, which causes death of alveolar cells in smoke-induced lung injury models [20]. Yoshida et al demonstrated that Rtp801 transcript and protein are overexpressed in human emphysematous lungs and in lungs of mice exposed to cigarette smoke. Mechanistically, they found that Rtp801 was necessary and sufficient for NF-kB activation in cultured pulmonary cells and, when artificially expressed in mouse lungs by gene transfection, the protein promoted NF-kB activation, alveolar inflammation, oxidative stress and apoptosis of alveolar septal cells. Experiments furthermore demonstrated that mice lacking Rtp801 by means of gene knock-out were protected against acute cigarette smoke-induced lung injury. Protection was associated with increased mTOR signaling. Furthermore, the authors found that Rtp801 knockout mice were protected against emphysema when exposed chronically to cigarette smoke [21]. The mechanism of pulmonary damage associated with Rtp801 involves not only NF-kB associated induction of inflammatory cytokines but also ceramide-dependent apoptotic pathways. Specifically, it was demonstrated that direct lung instillation of either RTP801 expression plasmid or ceramides in mice triggered alveolar cell apoptosis and oxidative stress. RTP801 overexpression up-regulated lung ceramide levels 2.6-fold as compared to administration of a control plasmid. In turn, instillation of lung ceramides doubled the lung content of RTP801. Cell sorting after lung tissue dissociation into single-cell suspension showed that ceramide triggers both endothelial and epithelial cell apoptosis in vivo. It may be possible that endothelial apoptosis triggers a cascade of enhanced hypoxia, which in turn further augments HIF-1 alpha activation, thus self-perpetuating expression of RTP801. Interestingly, mice lacking rtp801 were protected against ceramide-induced apoptosis of epithelial type II cells, but not type I or endothelial cells [22]. This is of interest for two reasons, firstly, epithelial type II cells are known to be capable of acting as "regenerative cells" in the lung, which start proliferating after various injury signals [23], and secondly, the ceramide apoptotic pathway is triggered by various inflammatory signals associated with COPD such as TNF-alpha produced by neutrophils and monocytes [24-26].

In some embodiments, the fibroblasts are used to suppress "danger" signaling. Globally, RTP801 may be seen as a damage "sensor" molecule, amongst which other molecules such as toll like receptors (TLRs), and other activators of innate immune system play similar roles [27]. For example, TLR2, TLR3, and TLR4 have been found to be expressed in airway smooth muscle cells, which were activated by ligands found in inflammatory conditions associated with COPD and pulmonary remodeling such as extracellular matrix degradation products [28]. A clinical study performed mini-bronchoalveolar lavage (mini-BAL) on ten nonsmoker subjects without COPD, six smokers without COPD, and fifteen smokers with COPD. COPD mini-BAL showed increased neutrophil numbers, reduced neutrophil apoptosis, which was associated with increased TLR4 expression, compared with those in nonsmoker subjects without COPD. Demonstrating the importance of TLR4 was that in vitro administration of blocking antibodies to TLR4 resulted in increased neutrophil apoptosis [29]. Specific genetic variants of TLR4 have been associated with development of COPD, thus suggesting this molecule to also be a link to initiation and progression of the inflammatory state of this condition [30]. (Tlr 4 activation in lung is deleterious, whereas TLR4 activation in fibroblasts renders fibroblast more anti-inflammatory.)

In addition to neutrophils, other cells of the innate immune system are associated with COPD. For example, natural killer (NK) cells have between found to be associated with initiation and progression of the disease. Wang et al performed a 124 patient study in smokers with COPD. They found systemic NK cell activation correlated with number of cigarettes smoked. Additionally, in induced sputum, the proportion of activated killer cells was related to disease state rather than current smoking status, with current and ex-smokers with COPD having significantly higher rates of activation than healthy smokers and healthy non-smokers [31]. NK activation is associated with production of cytotoxic factors such as granzyme, as well as various inflammatory cytokines including interferon gamma, which sensitize cells to inflammatory and immunologically mediated damage [32]. NK cell activation appears to be associated with recognition by the NK activating receptor NKG2D of the ligand RAET1ε, which is expressed on injured and stressed tissues. In fact, mice lacking NKG2D have been demonstrated to have a resistance to development of COPD-like pathology after exposure to cigarette smoke or viral infection [33]. While the natural function of NK cells in the lungs appears to be control of various infections [34], in the case of COPD it appears that these cells are "misguided" towards augmentation and self-perpetuation of the ongoing inflammatory cascade [35]. Thus in some embodiments of the invention, fibroblasts and/or exosomes thereof are utilized to suppress NK activity in COPD.

In particular embodiments, fibroblasts can generate T regulatory cells that suppress COPD. In specific embodiments of the disclosure, T cells are modulated by fibroblasts and/or exosomes thereof in order to inhibit, ameliorate, and in some cases reverse COPD. Contributions of adaptive immune cells to ongoing inflammatory processes has becoming increasingly recognized in situations such as ischemia/reperfusion injury [36], liver injury [37], and cancer [38], and the situation of COPD is no exception. Suggesting a role for T cells in COPD was an early study in 1987 in which T lymphocytes were found to be significantly present in lavage fluid of patients with COPD but not controls. Furthermore, numbers of T cells were significantly reduced in responders to thiol drug tiopronin [39]. Indeed, other studies have confirmed the presence of various types of T cells, both CD4 and CD8 are present in abnormally high levels in COPD patients as compared to controls, with smoking augmenting levels of these cells [40-43]. Suggestive of a possible autoimmune activity of intrapulmonary T cells came from studies showing activated state of T cells in lungs of COPD patients. A study by Glader et al examine peripheral blood lymphocytes from six never-smokers, eight smokers and 17 smokers with COPD. The number of lymphocytes per milliliter was higher in smokers than in never-smokers. No differences were found between the three groups in regard to proportions of lymphocyte populations, but the number of CD4+ T-cells in smokers was higher than in both never-smokers and COPD patients. The degree of T-cell activation was similar in all patient groups; however, a clear correlation between CD69 expression on CD4+ T-cells and lung function (FEV(1)% of predicted) was found when examining current smokers, with or without COPD [44]. Another study examined the Th1 associated transcription factor, STAT4, expression in lungs of patients with COPD. Th1 cells are associated with interferon gamma production and stimulation of inflammatory cascades, in part through macrophage activation and specifically stimulation of iNOS, as well as augmentation of NK activity. The study examined expression of STAT4, phospho-STAT4, IFN-gamma and T-box expressed in T-cells (T-bet) proteins in bronchial biopsies and bronchoalveolar lavage (BAL)-derived lymphocytes, obtained from 12 smokers with mild/moderate chronic obstructive pulmonary disease (COPD) (forced expiratory volume in one second (FEV1) 59+/−16% predicted), 14 smokers with normal lung function (FEV1 106+/−12% pred) and 12 nonsmoking subjects (FEV1 111+/−14% pred). In bronchial biopsies of COPD patients, the number of submucosal phospho-STAT4+ cells was increased (240 (22-406) versus 125 (0-492) versus 29 (0-511) cells mm(−2)) when compared with both healthy smokers and control nonsmokers, respectively. In smokers, phospho-STAT4+ cells correlated with the degree of airflow obstruction and the number of IFN-gamma+ cells. Similar results were seen in BAL (2.8 (0.2-5.9) versus 1.03 (0.09-1.6) versus 0.69 (0-2.3) lymphocytesxmL (−1)×10(3)). In all smokers who underwent lavage, phospho-STAT4+ lymphocytes correlated with airflow obstruction and the number of IFNgamma+ lymphocytes [45].

In addition to CD4 activation, activation of CD8 T cells has been reported in COPD. An investigation of bronchoscopy with airway lavages and endobronchial mucosal biopsy sampling was performed in 35 patients with COPD, 21 healthy never-smokers and 16 smokers with normal lung function. Epithelial CD8+ lymphocyte numbers were higher in the COPD group compared to never-smoking controls. Among gated CD3+ cells in BAL, the percentage of CD8+ NKG2D+ cells was enhanced in patients with COPD and smokers with normal lung function, compared to never-smokers. NKG2D is a receptor associated with stimulation of cytotoxic function by both NK cells and CD8 T cells. The percentage of CD8+CD69+ cells and cell surface expression of CD69 were enhanced in patients with COPD and smokers with normal lung function, compared to never-smokers [46]. Given that both NKG2D and CD69 are associated with activation of CD8 cells, it is reasonable to believe that COPD is associated with an abnormality in the activation status of these cells.

In addition to activation of CD4 and CD8 T cells, there appears to be a deficiency in the T cells that are required to suppress rampant T cell activation, the T regulatory (Treg) cells. Hou et al. examined blood samples from 57 never-smokers, 32 smokers with normal lung function and 66 patients with COPD, as well as bronchoalveolar lavage samples were taken from 12 never-smokers, 12 smokers and 18 patients with COPD. They found In peripheral blood, increased proportions of rTregs, aTregs and Fr III cells in smokers compared with never-smokers, whereas patients with COPD showed decreased rTregs and aTregs, and significantly increased Fr III cells compared with smokers. The changes in Treg subpopulations, with an overall decrease in the (aTreg+rTreg):(Fr III) ratio, indicated that immune homeostasis favoured inflammation and correlated with enhanced CD8 T-cell activation (r=−0.399, p<0.001) and forced expiratory volume in 1 s ($FEV_1$) % predicted value (r=0.435, p<0.001). The BAL (aTreg+rTreg):(Fr III) ratios displayed more robust correlations with $FEV_1$% predicted value (r=0.741, p<0.01) and activation of effector T cells (r=−0.763, p<0.001) [47]. Abnormalities of reduced Treg in COPD have also been described in animal models [48, 49].

In some embodiments of the disclosure, an individual in need of medical care, including having lung disease or at risk thereof, including for COPD, is administered an effective amount of fibroblasts and/or exosomes thereof. In further aspects, the individual is administered one or more additional follow-on doses of the fibroblasts. Follow-on doses can be administered at various time intervals depending on the patient's age, weight, ability to comply with physician instructions, clinical assessment, eosinophil count (blood or sputum eosinophils or eosinophilic cationic protein (ECP) measurement), or and other factors, including the judgment of the attending physician. The intervals between doses may be every week, every 2 weeks, every 3 weeks, 4 weeks, every 5 weeks, every 6 weeks, every 8 weeks, every 10 weeks, every 12 weeks, or longer intervals. In certain aspects, the intervals between doses can be every 4 weeks or every 8 weeks. In certain aspects, the intervals between doses can be every 4 weeks and every 8 weeks. In certain aspects, fibroblasts and/or exosomes thereof are administered with three four-week dosing intervals (i.e., on Day 0, Week 4, and Week 8) and then with eight-week dosing intervals (i.e., on Week 16, Week 24, Week 32, etc.).

In certain aspects, the individual is an individual with lung disease, such as a COPD patient, and a single dose or first dose is administered to the COPD patient shortly after the patient presents with an acute exacerbation, e.g., a mild, moderate or severe exacerbation. For example, the single or first dose of fibroblasts and/or exosomes thereof can be administered during the presenting clinic or hospital visit, or in the case of very severe exacerbations, within 1, 2, 3, 4, 5, 6, 7, or more days, e.g., 7 days of the acute exacerbation, allowing the patient's symptoms to stabilize prior to administration of fibroblast or exosomes thereof.

In some embodiments, at least two doses of fibroblasts and/or exosomes thereof are administered to the patient. In some embodiments, at least three doses, at least four doses, at least five doses, at least six doses, or at least seven doses are administered to the patient. In some embodiments, fibroblast or exosomes thereof is administered over the course of four weeks, over the course of eight weeks, over the course of twelve weeks, over the course of twenty-four weeks, over the course of forty-eight weeks, or over the course of a year or more.

The amount of fibroblasts and/or exosomes thereof to be administered to the patient can depend on various parameters such as the patient's age, weight, clinical assessment, eosinophil count (blood or sputum eosinophils, eosinophilic cationic protein (ECP) measurement, or eosinophil derived neurotoxin (EDN) measurement), or and other factors, including the judgment of the attending physician. In certain aspects, the dosage or dosage interval is not dependent on the eosinophil level. In certain embodiments, the patient is administered one or more doses of fibroblasts and/or exosomes thereof, for example wherein the dose is about 1-5 million cells per kilogram body weight.

The fibroblasts and/or exosomes thereof may be delivered in any suitable manner to the individual. In certain aspects, administration of fibroblasts and/or exosomes thereof according to the methods provided herein is through parenteral administration. For example, fibroblasts and/or exosomes thereof can be administered by intravenous infusion or by subcutaneous injection. In certain embodiments, fibroblasts and/or exosomes thereof can be administered by subcutaneous injection, intravenously, intranasally, intratracheally, intrarectally, intravaginally, and/or intradermally.

In certain aspects, fibroblasts and/or exosomes thereof are administered according to the methods provided herein in combination or in conjunction with additional therapies. Such therapies include, without limitation, corticosteroid therapy (including inhaled corticosteroids (ICS)), long-acting beta agonists (LABA, including long-acting (32 agonists), tiotropium, or other standard therapies. In certain aspects, benralizumab or an antigen-binding fragment thereof is administered according to the methods provided herein in combination or in conjunction with ICS and LABA, with LABA and LAMA, or with ICS, LABA, and LAMA.

In certain instances, administration of fibroblast and/or exosomes thereof decreases the intensity and/or frequency of COPD exacerbations including, for example, as measured by an exacerbation rate, an annual exacerbation rate, time to first exacerbation, and/or an annual rate of COPD exacerbations that are associated with an emergency room visit or hospitalization.

The methods provided herein can reduce exacerbation rates in COPD patients. In certain aspects, use of the methods provided herein, i.e., administration of fibroblast or exosomes thereof reduces the number of exacerbations experienced by the patient as compared to the number of exacerbations expected according to the patient's history, as compared to the average number of exacerbations expected in a comparable population of patients, or as compared to a comparable population treated with placebo over the same time period. In certain aspects, administration of fibroblast and/or exosomes thereof reduces the number of exacerbations in COPD patients with eosinophil counts of at least 200 eosinophils/μL prior to the administration (as one example, as measured routinely from the blood). In certain aspects, administration of fibroblast or exosomes thereof reduces the number of exacerbations in COPD patients with eosinophil counts of at least 300 eosinophils/μL prior to the administration. In certain aspects, administration of fibroblast or exosomes thereof reduces the number of exacerbations in COPD patients with eosinophil counts of at least 400 eosinophils/μL prior to the administration.

In certain aspects, administration of fibroblasts and/or exosomes thereof reduces the number of exacerbations in COPD patients with severe COPD as defined by the Global Initiative for Chronic Obstructive Lung Disease (GOLD), Global strategy for the diagnosis, management, and prevention of chronic obstructive pulmonary disease (updated 2009). In certain aspects, administration of fibroblast or exosomes thereof reduces the number of exacerbations in COPD patients with very severe COPD as defined by the GOLD. In certain aspects, administration of fibroblast and/or exosomes thereof reduces the number of exacerbations in COPD patients with severe or very severe COPD as defined by the GOLD. In certain aspects, administration of fibroblast and/or exosomes thereof reduces the number of exacerbations in COPD patients who are receiving corticosteroids (e.g., inhaled corticosteroids (ICS), long-acting beta-agonists (LABA) (e.g., long-acting beta2-agonists), and/or tiotropium.

In certain aspects, administration of fibroblasts and/or exosomes thereof reduces exacerbations by at least about 15%, by at least about 20%, by at least about 25%, by at least about 30%, at least about 35%, at least about 40%, at least about 45%, at least about 50%, or at least about 55% (for example, as measured by the number of episodes). In some embodiments, exacerbations are reduced about 34%, about 47%, or about 57%. The exacerbations can be reduced, for example, within a year from the first administration fibroblast or exosomes thereof.

In certain aspects of the methods provided herein, i.e., administration of fibroblasts and/or exosomes thereof reduces exacerbation rates within 4 weeks of the administration, within 8 weeks, within 12 weeks, within 16 weeks, within 20 weeks, within 24 weeks, within 28 weeks, within 32 weeks, within 36 weeks, within 40 weeks, within 44 weeks, within 48 weeks, or within 52 weeks.

The methods provided herein can reduce exacerbation rates in COPD patients with severe or very severe COPD (as defined by GOLD), for example by at least 40% or by about 47%. The methods provided herein can reduce "annual exacerbation rates" in COPD patients.

The methods provided herein can increase the time to a first COPD exacerbation after a first administration of fibroblast and/or exosomes thereof, as compared to after a first administration of placebo or with no placebo or treatment. In some instances, administration of fibroblasts and/sor exosomes thereof decreases the likelihood of a COPD exacerbation (e.g., within 52 weeks of a first administration of fibroblast or exosomes thereof) as compared to the likelihood of a COPD exacerbation after treatment with placebo or with no placebo or treatment. In some instances, administration of fibroblasts and/or exosomes thereof decreases the annual rate of COPD exacerbations that are associated with an emergency room or hospitalization as compared to administration of placebo or with no placebo or treatment.

In certain instances, administration of fibroblasts and/or exosomes thereof improves the pulmonary function in a COPD patient, for example, as measured by forced expiratory volume in one second ($FEV_1$) or forced vital capacity.

The methods provided herein can increase forced expiratory volume in one second ($FEV_1$) in COPD patients. An increase can be measured based on the expected $FEV_1$ based on a large patient population, on the $FEV_1$ measured in a control population, or on the individual patient's $FEV_1$ prior to administration. In certain aspects, use of the methods provided herein, i.e., administration of fibroblasts and/or exosomes thereof, can increase the $FEV_1$, as compared to the patient's baseline $FEV_1$. In some embodiments, the increased $FEV_1$ is pre-bronchodilator $FEV_1$. In some embodiments, the increased $FEV_1$ is post-bronchodilator $FEV_1$. In some embodiments, the increased $FEV_1$ is pre-bronchodilator $FEV_1$ and post-bronchodilator $FEV_1$.

The FEV (e.g., the pre-bronchodilator and/or post-bronchodilator $FEV_1$) can be increased, for example, within a certain time period from the first administration of fibroblasts and/or exosomes thereof. For use in the disclosure, a "bronchodilator," as used herein, refers to any drug that widens or dilates the bronchi and bronchioles or air passages of the lungs, decreases resistance in the respiratory airway, and/or eases breathing by relaxing bronchial smooth muscle. For example, bronchodilators include short- and long-acting beta2-agonists such as albuterol/salbutamol and other drugs commonly used to treat asthma. The method and compositions of the present disclosure may increase the $FEV_1$ within 1-24 hours, 1-7 days, 1-4 weeks, 1-12 months, or one or more years after the first administration of fibroblasts and/or exosomes thereof In certain embodiments of the disclosure, the methods provided herein can increase $FEV_1$ by at least 5%, at least 6%, at least 7%, at least 8%, at least 9%, at least 10%, at least 11%, at least 12%, or more. In certain aspects, the methods provided herein can increase $FEV_1$ by about 12%. In certain aspects, the methods provided herein can increase pre-bronchodilator $FEV_1$ by at least 5%, at least 6%, at least 7%, at least 8%, at least 9%, at least 10%, at least 11%, at least 12% or more. In certain aspects, the methods provided herein can increase pre-bronchodilator $FEV_1$ by about 12%.

In certain aspects, the methods provided herein can increase $FEV_1$ by at least 5%. In certain aspects, the methods provided herein can increase $FEV_1$ by about 7%. In certain aspects, the methods provided herein can increase post-bronchodilator $FEV_1$ by at least 5%. In certain aspects, the methods provided herein can increase post-bronchodilator $FEV_1$ by about 7%.

In certain aspects, the methods provided herein can increase pre-bronchodilator and post-bronchodilator $FEV_1$ by at least 5%, 6%, 7%, 8%, 9%, 10%, 11%, 12%, or more. In certain aspects, the methods provided herein can increase pre-bronchodilator $FEV_1$ by at least 10% and post-bronchodilator $FEV_1$ by at least 5%. In certain aspects, the methods provided herein can increase pre-bronchodilator $FEV_1$ by about 12% and post-bronchodilator $FEV_1$ by about 7%. As provided herein, administration of fibroblasts and/or exosomes thereof can also increase the percent predicted $FEV_1$ in COPD patients e.g., pre-bronchodilator and/or post-bronchodilator. By way of example, the percent predicted $FEV_1$ can increase by about 3.0, about 3.5, about 4.0, or about 4.5.

The methods provided herein can increase $FEV_1$ in COPD patients with blood eosinophil counts of at least 200 eosinophils/μL, or in patients receiving corticosteroids (e.g., inhaled corticosteroids (ICS), long-acting beta-agonists (LABA) (e.g., long-acting beta2-agonists), and/or tiotropium. In certain aspects, the methods provided herein can increase FEV.sub.1 in such patients by at least 10% or by at least 15%. In certain aspects, the methods provided herein can increase pre-bronchodilator $FEV_1$ in such patients by at least 10% or by at least 15%. In certain aspects, the methods provided herein can increase post-bronchodilator $FEV_1$ in such patients by about 10%. In certain aspects, the methods provided herein can increase pre-bronchodilator $FEV_1$ and post-bronchodilator $FEV_1$ in such patients by at least 10%. In certain aspects, the methods provided herein can increase pre-bronchodilator $FEV_1$ in such patients by at least 15% and post-bronchodilator $FEV_1$ in such patients by at least 10%. The methods provided herein can increase $FEV_1$ in COPD patients with blood eosinophil counts of at least 300 eosinophils/μL or in COPD patients with severe or very severe COPD as defined by the Global Initiative for Chronic Obstructive Lung Disease (GOLD). In certain aspects, the methods provided herein can increase $FEV_1$ in such patients by at least 15% or by at least 20%. In certain aspects, the methods provided herein can increase pre-bronchodilator $FEV_1$ in such patients by at least 15% or by at least 20%. In certain aspects, the methods provided herein can increase post-bronchodilator $FEV_1$ in such patients by about 15%. In certain aspects, the methods provided herein can increase pre-bronchodilator $FEV_1$ and post-bronchodilator $FEV_1$ in such patients by at least 15%. In certain aspects, the methods provided herein can increase pre-bronchodilator $FEV_1$ in such patients by at least 20% and post-bronchodilator $FEV_1$ in such patients by at least 15%.

In certain aspects, use of the methods provided herein, i.e., administration of fibroblasts and/or exosomes thereof, increases the $FEV_1$ within 4 weeks, within 8 weeks, within 12 weeks, within 16 weeks, within 20 weeks, within 24 weeks, within 28 weeks, within 32 weeks, within 36 weeks, within 40 weeks, within 44 weeks, within 48 weeks, within 52 weeks, or within 56 weeks or more. In certain aspects, administration of fibroblast or exosomes thereof improves $FEV_1$ within 52 weeks of a first administration of the fibroblast or exosomes thereof. Use of the methods provided herein can increase $FEV_1$ by at least 0.05 L, at least 0.1 L, at least 0.13 L, at least 0.15 L, at least 0.20 L, at least 0.21 L, at least 0.22 L, at least 0.23 L, at least 0.24 L, or at least 0.25 L, at least 0.30 L, at least 0.35 L, at least 0.40 L, at least 0.45 L, or at least 0.50 L over the 56-week period.

The methods provided herein can increase forced vital capacity (FVC) in COPD patients. An increase can be measured based on the expected FVC based on a large patient population, on the FVC measured in a control population, or on the individual patient's FVC prior to administration. In certain aspects, use of the methods provided herein, i.e., administration of fibroblast or exosomes thereof, can increase the FVC, as compared to the patient's baseline FVC. In some embodiments, the increased FVC is pre-bronchodilator FVC. In some embodiments, the increased FVC is post-bronchodilator FVC. In some embodiments, the increased FVC is pre-bronchodilator FVC and post-bronchodilator FVC. The FVC (e.g., the pre-bronchodilator and/or post-bronchodilator FVC) can be increased, for example, within a year from the first administration of fibroblast or exosomes thereof.

In certain aspects, the methods provided herein can increase FVC by at least 3%. In certain aspects, the methods provided herein can increase pre-bronchodilator FVC by at least 2%, at least 3%, at least 5% or at least 10%. In certain aspects, the methods provided herein can increase post-bronchodilator FVC by at least 2%, at least 3%, at least 5% or at least 10%. In certain aspects, the methods provided herein can increase pre-bronchodilator and post-bronchodilator FVC by at least 2%, at least 3%, at least 5% or at least 10%. In certain aspects, use of the methods provided herein, i.e., administration of fibroblasts and/or exosomes thereof, increases FVC within 4 weeks, within 8 weeks, within 12 weeks, within 16 weeks, within 20 weeks, within 24 weeks, within 28 weeks, within 32 weeks, within 36 weeks, within 40 weeks, within 44 weeks, within 48 weeks, within 52 weeks, or within 56 weeks or more.

In certain instances, administration of fibroblasts and/or exosomes thereof improves respiratory symptoms in a COPD patient, for example, as measured by the Baseline/Transitional Dyspnea Index (BDI/TDI) and/or the Exacerbations of Chronic Pulmonary Disease Tool-Respiratory Symptoms (E-RS).

Provided herein are also methods for improving respiratory symptoms as measured by the Baseline/Transitional Dyspnea Index (TDI). For example, administration of fibroblast or exosomes thereof can improve (increase) a COPD patient's BDI score by at least 1, at least 2, or at least 3 and/or result in a positive TDI score. The BDI/TDI score can be improved, for example, within a year from the first administration of fibroblast or exosomes thereof.

In certain aspects, use of the methods provided herein, i.e., administration of fibroblasts and/or exosomes thereof, improves a BDI/TDI score within 4 weeks, within 8 weeks, within 12 weeks, within 16 weeks, within 20 weeks, within 24 weeks, within 28 weeks, within 32 weeks, within 36 weeks, within 40 weeks, within 44 weeks, within 48 weeks, within 52 weeks, or within 56 weeks or more.

Provided herein are also methods for improving respiratory symptoms as measured by the Exacerbations of Chronic Pulmonary Disease Tool-Respiratory Symptoms (E-RS). For example, administration of fibroblast or exosomes thereof can improve (decrease) a COPD patient's E-RS score by least 3, at least 4, at least 6, at least 7, at least 8, at least 9, or at least 10. The E-RS score can be improved, for example, within a year from the first administration of fibroblasts and/or exosomes thereof.

In certain aspects, use of the methods provided herein, i.e., administration of fibroblasts and/or exosomes thereof, improves a E-RS score within 1 week, 2 weeks, 3 weeks, 4 weeks, within 8 weeks, within 12 weeks, within 16 weeks, within 20 weeks, within 24 weeks, within 28 weeks, within 32 weeks, within 36 weeks, within 40 weeks, within 44 weeks, within 48 weeks, within 52 weeks, or within 56 weeks or more.

In certain instances, administration of fibroblast or exosomes thereof improves the health status and/or health-related quality of life in a COPD patient, for example, as measured by the Saint George's Respiratory Questionnaire (SGRQ), the COPD-Specific Saint George's Respiratory Questionnaire (SGRQ-C), and/or the COPD assessment tool (CAT).

Provided herein are methods for improving one or more COPD symptoms, e.g., as assessed using a COPD questionnaire such as the Saint George's Respiratory Questionnaire (SGRQ). For example, administration of fibroblast or exosomes thereof can improve a patient's SGRQ score by at least 3, at least 4, at least 6, at least 7, at least 8, at least 9, or at least 10. The SGRQ score can be improved, for example, within a year from the first administration of fibroblast or exosomes thereof.

In certain aspects, use of the methods provided herein, i.e., administration of fibroblasts and/or exosomes thereof, improves a SGRQ score within 4 weeks, within 8 weeks, within 12 weeks, within 16 weeks, within 20 weeks, within 24 weeks, within 28 weeks, within 32 weeks, within 36 weeks, within 40 weeks, within 44 weeks, within 48 weeks, within 52 weeks, or within 56 weeks or more. In certain aspects, administration of fibroblast or exosomes thereof improves an SGRQ score within 52 weeks of a first administration of the fibroblast or exosomes thereof.

Provided herein are also methods for improving COPD symptoms, e.g., as assessed using a COPD questionnaire such as the COPD-Specific Saint George's Respiratory Questionnaire (SGRQ-C). For example, administration of fibroblast or exosomes thereof can improve a COPD patient's SGRQ-C (symptom) score by at least 3, at least 4, at least 6, at least 7, at least 8, at least 9, or at least 10. The SGRQ-C (symptom) score can be improved, for example, within a year from the first administration of fibroblast or exosomes thereof.

In certain aspects, use of the methods provided herein, i.e., administration of fibroblasts and/or exosomes thereof, improves a SGRQ-C (symptom) score within 1 week, 2 weeks, 3 weeks, 4 weeks, within 8 weeks, within 12 weeks, within 16 weeks, within 20 weeks, within 24 weeks, within 28 weeks, within 32 weeks, within 36 weeks, within 40 weeks, within 44 weeks, within 48 weeks, within 52 weeks, or within 56 weeks or more.

Provided herein are also methods for improving COPD symptoms, e.g., as assessed using the COPD assessment tool (CAT). For example, administration of fibroblast or exosomes thereof can improve (decrease) a COPD patient's CAT score by least 3, at least 4, at least 6, at least 7, at least 8, at least 9, or at least 10. The CAT score can be improved (decreased), for example, within a year from the first administration of fibroblast or exosomes thereof.

In certain aspects, use of the methods provided herein, i.e., administration of fibroblasts and/or exosomes thereof, improves (decreases) a CAT score within 1 week, 2 weeks, 3 weeks, 4 weeks, within 8 weeks, within 12 weeks, within 16 weeks, within 20 weeks, within 24 weeks, within 28 weeks, within 32 weeks, within 36 weeks, within 40 weeks, within 44 weeks, within 48 weeks, within 52 weeks, or within 56 weeks or more.

In certain aspects, use of the methods provided herein, i.e., administration of fibroblast or exosomes thereof, reduces nocturnal awakenings.

In certain aspects, use of the methods provided herein, i.e., administration of fibroblast or exosomes thereof, reduces the use of rescue medication.

In certain aspects, use of the methods provided herein, i.e., administration of fibroblast or exosomes thereof, reduces the severity, frequency, and/or duration of EXACT-PRO defined events.

In certain aspects, use of the methods provided herein, i.e., administration of fibroblast or exosomes thereof, reduces COPD-specific resource utilization. For example, administration of fibroblast or exosomes thereof can reduce unscheduled physician visits, unscheduled phone calls to physicians, and/or use of other COPD medications.

In certain aspects, use of the methods provided herein, i.e., administration of fibroblast or exosomes thereof to a COPD patient, increases forced expiratory volume in one second ($FEV_1$), increases forced vital capacity (FVC), reduces COPD exacerbation rate, and/or improves a COPD questionnaire score (e.g., the COPD control questionnaire).

In certain aspects, use of the methods provided herein, i.e., administration of fibroblast or exosomes thereof to a COPD patient, decreases annual COPD exacerbation rate, improves SGRQ scores, and increases $FEV_1$ (e.g., in COPD patients with a baseline blood eosinophil count of 300/μL).

In certain aspects, the COPD patient was prescribed or has been and/or is currently using corticosteroids (e.g., inhaled corticosteroids (ICS)), long-acting beta-agonists (LABA, e.g., long-acting beta2-agonists), and tiotropium prior to the administration of fibroblast or exosomes thereof. In certain aspects, the COPD patient is treated with corticosteroids (e.g., ICS), LABA (e.g., long-acting beta2-agonists), tiotropium, and fibroblast or exosomes thereof. In certain aspects, the COPD patient is treated with ICS and LABA. In certain aspects, the COPD patient is treated with LABA and long-acting muscarinic antagonist (LAMA). In certain aspects, the COPD patient is treated with ICS and LABA or with LABA and LAMA. In certain aspects, the COPD patient is treated with ICS, LABA, and LAMA.

In certain aspects of the methods provided herein, the patient has a history of COPD exacerbation(s). In certain aspects, the history of exacerbations comprises at least one exacerbation in the year prior to the administration of fibroblast or exosomes thereof. In certain aspects, the patient has a forced expiratory volume (FEV.sub.1) of less than 80% predicted value prior to the administration. In certain aspects, the patient has an FEV.sub.1/FVC of less than 0.70 prior to the administration.

In one embodiment of the disclosure, exosomes are purified from fibroblast cells by obtaining a fibroblast cell-conditioned medium, concentrating the fibroblast cell-conditioned medium, subjecting the concentrated fibroblast cell-conditioned medium to size exclusion chromatography, selecting UV absorbent fractions at 220 nm, and concentrating fractions containing exosomes.

Exosomes, also referred to as "particles" may comprise vesicles or a flattened sphere limited by a lipid bilayer. The particles may comprise diameters of 40-100 nm. The particles may be formed by inward budding of the endosomal membrane. The particles may have a density of about 1.13-1.19 g/ml and may float on sucrose gradients. The particles may be enriched in cholesterol and sphingomyelin, and lipid raft markers such as GM1, GM3, flotillin and the src protein kinase Lyn. The particles may comprise one or more proteins present in fibroblast or fibroblast-conditioned medium (fibroblast-CM) such as a protein characteristic or specific to the fibroblast or fibroblast-CM. They may comprise RNA, for example miRNA. The particles may possess one or more genes or gene products found in fibroblast or medium that is conditioned by culture of fibroblasts. The particle may comprise molecules secreted by the fibroblast. Such a particle, and combinations of any of the molecules comprised therein, including in particular proteins or polypeptides, may be used to supplement the activity of, or in place of, the fibroblast and/or medium conditioned by the fibroblasts for the purpose of, for example, treating or preventing a lung disease. The particle may comprise a cytosolic protein found in cytoskeletons, e.g. tubulin, actin and actin-binding proteins; intracellular membrane fusions and transport, e.g. annexins and rab proteins; signal transduction proteins, e.g. protein kinases, 14-3-3 and heterotrimeric G proteins; metabolic enzymes e.g. peroxidases, pyruvate and lipid kinases, and enolase-1 and the family of tetraspanins e.g. CD9, CD63, CD81 and CD82. In particular, the particle may comprise one or more tetraspanins. The particles may comprise mRNA and/or microRNA. In one embodiment, fibroblast exosomes, or particles may be produced by culturing fibroblast cells in a medium to condition it. The fibroblast cells may comprise human umbilical tissue-derived cells which possess markers selected from the group consisting of CD90, CD73, CD105, and a combination thereof. The medium may comprise DMEM. The DMEM may be such that it does not comprise phenol red. The medium may be supplemented with insulin, transferrin, or selenoprotein (ITS), or any combination thereof. It may comprise FGF2. It may comprise PDGF AB. The concentration of FGF2 may be about 5 ng/ml FGF2 in the exosome, for example. The concentration of PDGF AB may be about 5 ng/ml. The medium may comprise glutamine-penicillin-streptomycin or b-mercaptoethanol, or any combination thereof.

The cells may be cultured for about 1, 2, 3, 4, 5, 6, 7, 8, 9, 10 days or more, for example about 3 days. The conditioned medium may be obtained by separating the cells from the medium. The conditioned medium may be centrifuged, for example at 500 g. It may be concentrated by filtration through a membrane. The membrane may comprise a >1000 kDa membrane, as one example. The conditioned medium may be concentrated about 50 times or more, including prior to use and/or storage. The conditioned medium may be subject to liquid chromatography such as HPLC. The conditioned medium may be separated by size exclusion. Any size exclusion matrix such as Sepharose may be used. As an example, a TSK Guard column SWXL, 6×40 mm or a TSK gel G4000 SWXL, 7.8×300 mm may be employed. The eluent buffer may comprise any physiological medium such as saline. It may comprise 20 mM phosphate buffer with 150 mM of NaCl at pH 7.2. The chromatography system may be equilibrated at a flow rate of 0.5 ml/min. The elution mode may be isocratic. UV absorbance at 220 nm may be used to track the progress of elution. Fractions may be examined for dynamic light scattering (DLS) using a quasi-elastic light scattering (QELS) detector. Fractions that are found to exhibit dynamic light scattering may be retained. For example, a fraction which is produced by the general method as described above, and which elutes with a retention time of 11-13 minutes, such as 12 minutes, is found to exhibit dynamic light scattering. The $r_h$ of particles in this peak is about 45-55 nm. Such fractions may comprise fibroblast particles such as exosomes.

Embodiments of the disclosure include methods having diagnosis of lung disease as a step, although in some cases diagnosis occurs outside the methods. Diagnosis may involve imaging tests, blood tests, and/or lung function tests. Specifically, one may utilize spirometry that is a noninvasive test to assess lung function. Imaging tests include a chest X-ray and/or CT scan. An arterial blood gas test may be utilized that involves taking a blood sample from an artery to measure blood oxygen, carbon dioxide, and other important levels.

The individual may be subjected to combination therapy including the inventive methods and compositions provided herein in addition to short- and long-acting beta2-agonists, anticholinergics, one or more corticosteroids, one or more phosphodiesterase-4 inhibitors, supplemental oxygen therapy, and/or surgery, for example. The therapy or therapies in addition to the fibroblasts and/or exosomes thereof may be given at the same time and/or at different times. They may be given by the same route and/or different routes. They may be given for the same or different durations. One or multiple doses of the therapy of the disclosure may be provided with only one dose of the one or more other therapies, and vice versa.

III. Fibroblasts and Modifications and Preparations Thereof

An effective amount of fibroblasts are prepared and provided to an individual in need thereof. The fibroblasts may be autologous or allogeneic with respect to the individual being treated.

In specific embodiments, the fibroblasts are present in a culture, whether for storage and/or preparation. Various terms are used to describe cells in culture. Cell culture refers generally to cells taken from a living organism and grown under controlled condition ("in culture" or "cultured"). A primary cell culture is a culture of cells, tissues, or organs taken directly from an organism(s) before the first subculture. Cells are expanded in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

A cell line is a population of cells formed by one or more sub-cultivations of a primary cell culture. Each round of sub-culturing is referred to as a passage. When cells are sub-cultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

In some embodiments, the fibroblasts are comprised in a conditioned medium or have been in or exposed to a conditioned medium. A conditioned medium is a medium in which a specific cell or population of cells has been cultured, and then removed. When cells are cultured in a medium, they may secrete one or more cellular factors that can provide trophic support to other cells or have another function. Generally, a trophic factor is defined as a substance that promotes or at least supports, survival, growth, proliferation and/or maturation of a cell, or stimulates increased activity of a cell. Such trophic factors include, but are not limited to hormones, cytokines, extracellular matrix (ECM), proteins, vesicles, antibodies, and granules. The medium containing the cellular factors is the conditioned medium. The fibroblasts may secrete one or more factors or entities (Such as exosomes) that are utilized for a medical purpose either alone or in conjunction with one or more other components.

As used herein, the term Growth Medium generally refers to a medium sufficient for the culturing of fibroblast cells of any kind. In particular, one medium for the culturing of the cells of the invention herein comprises Dulbecco's Modified Essential Media (also abbreviated DMEM herein). Particularly preferred is DMEM-low glucose (also DMEM-LG herein) (Invitrogen, Carlsbad, Calif.). The DMEM-low glucose is preferably supplemented with 15% (v/v) fetal bovine serum (e.g. defined fetal bovine serum, Hyclone, Logan Utah), antibiotics/antimycotics (preferably penicillin (100 Units/milliliter), streptomycin (100 milligrams/milliliter), and amphotericin B (0.25 micrograms/milliliter), (Invitrogen, Carlsbad, Calif.)), and 0.001% (v/v) 2-mercaptoethanol (Sigma, St. Louis Mo.). In some cases different growth media are used, or different supplementations are provided, and these are normally indicated in the text as supplementations to Growth Medium.

Also relating to the present disclosure, the term standard growth conditions, as used herein refers to culturing of cells at 37° C., in a standard atmosphere comprising 5% $CO_2$. Relative humidity is maintained at about 100%. While foregoing the conditions are useful for culturing, it is to be understood that such conditions are capable of being varied by the skilled artisan who will appreciate the options available in the art for culturing cells, for example, varying the temperature, $CO_2$, relative humidity, oxygen, growth medium, and the like.

The cells may be prepared for administration in a pharmaceutically acceptable carrier, for example a sterile saline isotonic solution. In some embodiments, the pharmaceutically acceptable carrier may comprise one or more additional agents, such as FAS ligand, IL-2R, IL-1 Ra, IL-2, IL-4, IL-8, IL-10, IL-20, IL-35, HLA-G, PD-L1, 1-309, IDO, iNOS, CD200, Galectin 3, sCR1, arginase, PGE-2, aspirin, atorvastatin, fluvastatin, lovastatin, pravastatin, rosuvastatin, simvastatin, pitavastatin, n-acetylcysteine, rapamycin, IVIG, naltrexone, TGF-beta, VEGF, PDGF, CTLA-4, anti-CD45RB antibody, hydroxychloroquine, leflunomide, auranofin, dicyanogold, sulfasalazine, methotrexate, glucocorticoids, etanercept, adalimumab, abatacept, anakinra, certolizumab, Etanercept-szzs, golimumab, infliximab, rituximab, tocilizumab, cyclosporine, IFN-gamma, everolimus, rapamycin, VEGF, FGF-1, FGF-2, angiopoietin, HIF-1-alpha, or a combination thereof.

In one embodiment of the disclosure, fibroblasts are administered to a subject by any suitable route, including by injection (such as intramuscular injection), including in hypoxic areas. Suitable routes include intravenous, subcutaneous, intrathecal, oral, intrarectal, intrathecal, intraomentral, intraventricular, intrahepatic, and intrarenal.

In certain embodiments, fibroblasts may be derived from tissues comprising skin, heart, blood vessels, bone marrow, skeletal muscle, liver, pancreas, brain, adipose tissue, foreskin, placental, and/or umbilical cord. In specific embodiments, the fibroblasts are placental, fetal, neonatal or adult or mixtures thereof.

The number of administrations of cells to an individual will depend upon the factors described herein at least in part and may be optimized using routine methods in the art. In specific embodiments, a single administration is required. In other embodiments, a plurality of administration of cells is required. It should be appreciated that the system is subject to variables, such as the particular need of the individual, which may vary with time and circumstances, the rate of loss of the cellular activity as a result of loss of cells or activity of individual cells, and the like. Therefore, it is expected that each individual could be monitored for the proper dosage, and such practices of monitoring an individual are routine in the art.

In some embodiments, the cells are subjected to one or more media compositions that comprises, consists of, or consists essentially of Roswell Park Memorial Institute (RPMI-1640), Dublecco's Modified Essential Media (DMEM), Eagle's Modified Essential Media (EMEM), Optimem, Iscove's Media, or a combination thereof.

IV. Kits of the Disclosure

Certain aspects of the present disclosure also concern kits containing compositions of the disclosure or compositions to implement methods of the disclosure. In some embodiments, kits can be used to provide fibroblast regenerative cells, population thereof, progeny thereof or conditioned media thereof. In some cases, kits include one or more reagents for producing and/or identifying fibroblast regenerative cells.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

In certain aspects, negative and/or positive control agents are included in some kit embodiments. The control molecules can be used to verify the enhance regenerative activity of fibroblast cells.

Kits may comprise a container with a label. Suitable containers include, for example, bottles, vials, and test tubes. The containers may be formed from a variety of materials such as glass or plastic. The container may hold a composition which includes a probe that is useful for prognostic or non-prognostic applications, such as described above. The label on the container may indicate that the composition is used for a specific prognostic or non-prognostic application, and may also indicate directions for either in vivo or in vitro use, such as those described above. The kit may comprise the container described above and one or more other containers comprising materials desirable from a commercial and user standpoint, including buffers, diluents, filters, needles, syringes, and package inserts with instructions for use.

The kit may or may not comprise one or more additional therapies for lung disease, including short- and long-acting beta2-agonist(s), anticholinergic(s), one or more corticosteroid(s), one or more phosphodiesterase-4 inhibitor(s), theophylline, and so forth.

The kit may or may not comprise one or more devices and/or reagents for diagnosis of lung disease.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

1. Mapel, D. W., et al., *Identifying and characterizing COPD patients in US managed care. A retrospective, cross-sectional analysis of administrative claims data.* BMC Health Sery Res, 2011. 11: p. 43.
2. Ejiofor, S. and A. M. Turner, *Pharmacotherapies for COPD.* Clin Med Insights Circ Respir Pulm Med, 2013. 7: p. 17-34.
3. Miravitlles, M., et al., *Costs of chronic obstructive pulmonary disease in relation to compliance with guidelines: a study in the primary care setting.* Ther Adv Respir Dis, 2013. 7(3): p. 139-50.
4. Holloway, R. A. and L. E. Donnelly, *Immunopathogenesis of chronic obstructive pulmonary disease.* Curr Opin Pulm Med, 2013. 19(2): p. 95-102.
5. Motz, G. T., et al., *Persistence of lung CD8 T cell oligoclonal expansions upon smoking cessation in a mouse model of cigarette smoke-induced emphysema.* J Immunol, 2008. 181(11): p. 8036-43.
6. Maeno, T., et al., *CD8+ T Cells are required for inflammation and destruction in cigarette smoke-induced emphysema in mice.* J Immunol, 2007. 178(12): p. 8090-6.
7. Woodruff, P. G., et al., *A distinctive alveolar macrophage activation state induced by cigarette smoking.* Am J Respir Crit Care Med, 2005. 172(11): p. 1383-92.
8. Stefanska, A. M. and P. T. Walsh, *Chronic obstructive pulmonary disease: evidence for an autoimmune component.* Cell Mol Immunol, 2009. 6(2): p. 81-6.
9. Gonzalez-Rey, E., et al., *Human adipose-derived mesenchymal stem cells reduce inflammatory and T cell responses and induce regulatory T cells in vitro in rheumatoid arthritis.* Ann Rheum Dis. 69(1): p. 241-8.
10. Lepelletier, Y., et al., *Galectin-1 and Semaphorin-3A are two soluble factors conferring T cell immunosuppression to bone marrow mesenchymal stem cell.* Stem Cells Dev, 2009.
11. Tsyb, A. F., et al., *In vitro inhibitory effect of mesenchymal stem cells on zymosan-induced production of reactive oxygen species.* Bull Exp Biol Med, 2008. 146(1): p. 158-64.
12. Sun, L., et al., *Mesenchymal stem cell transplantation reverses multiorgan dysfunction in systemic lupus erythematosus mice and humans.* Stem Cells, 2009. 27(6): p. 1421-32.
13. Aslam, M., et al., *Bone marrow stromal cells attenuate lung injury in a murine model of neonatal chronic lung disease.* Am J Respir Crit Care Med, 2009. 180(11): p. 1122-30.
14. van Haaften, T., et al., *Airway delivery of mesenchymal stem cells prevents arrested alveolar growth in neonatal lung injury in rats.* Am J Respir Crit Care Med, 2009. 180(11): p. 1131-42.
15. Seimetz, M., et al., *Inducible NOS inhibition reverses tobacco-smoke-induced emphysema and pulmonary hypertension in mice.* Cell, 2011. 147(2): p. 293-305.
16. Iho, S., et al., *Nicotine induces human neutrophils to produce IL-8 through the generation of peroxynitrite and subsequent activation of NF-kappaB.* J Leukoc Biol, 2003. 74(5): p. 942-51.
17. Tanni, S. E., et al., *Smoking status and tumor necrosis factor-alpha mediated systemic inflammation in COPD patients.* J Inflamm (Lond), 2010. 7: p. 29.
18. Weathington, N. M., et al., *A novel peptide CXCR ligand derived from extracellular matrix degradation during airway inflammation.* Nat Med, 2006. 12(3): p. 317-23.
19. Xu, X., et al., *A self-propagating matrix metalloprotease-9 (MMP-9) dependent cycle of chronic neutrophilic inflammation.* PLoS One, 2011. 6(1): p. e15781.
20. Shoshani, T., et al., *Identification of a novel hypoxia-inducible factor 1-responsive gene, RTP801, involved in apoptosis.* Mol Cell Biol, 2002. 22(7): p. 2283-93.
21. Yoshida, T., et al., *Rtp801, a suppressor of mTOR signaling, is an essential mediator of cigarette smoke-induced pulmonary injury and emphysema.* Nat Med, 2010. 16(7): p. 767-73.
22. Kamocki, K., et al., *RTP801 is required for ceramide-induced cell-specific death in the murine lung.* Am J Respir Cell Mol Biol, 2013. 48(1): p. 87-93.
23. Buckley, S., et al., *The milieu of damaged alveolar epithelial type 2 cells stimulates alveolar wound repair by endogenous and exogenous progenitors.* Am J Respir Cell Mol Biol, 2011. 45(6): p. 1212-21.
24. Medler, T. R., et al., *Apoptotic sphingolipid signaling by ceramides in lung endothelial cells.* Am J Respir Cell Mol Biol, 2008. 38(6): p. 639-46.

25. Thon, L., et al., *Ceramide mediates caspase-independent programmed cell death.* FASEB J, 2005. 19(14): p. 1945-56.
26. Chung, K. F., *Cytokines as targets in chronic obstructive pulmonary disease.* Curr Drug Targets, 2006. 7(6): p. 675-81.
27. Tuder, R. M. and T. Yoshida, *Stress responses affecting homeostasis of the alveolar capillary unit.* Proc Am Thorac Soc, 2011. 8(6): p. 485-91.
28. Sukkar, M. B., et al., *Toll-like receptor 2, 3, and 4 expression and function in human airway smooth muscle.* J Allergy Clin Immunol, 2006. 118(3): p. 641-8.
29. Pace, E., et al., *TLR4 upregulation underpins airway neutrophilia in smokers with chronic obstructive pulmonary disease and acute respiratory failure.* Hum Immunol, 2011. 72(1): p. 54-62.
30. Speletas, M., et al., *Association of TLR4-T3991 polymorphism with chronic obstructive pulmonary disease in smokers.* Clin Dev Immunol, 2009. 2009: p. 260286.
31. Wang, J., et al., *Differential activation of killer cells in the circulation and the lung: a study of current smoking status and chronic obstructive pulmonary disease (COPD).* PLoS One, 2013. 8(3): p. e58556.
32. Tassi, I., J. Klesney-Tait, and M. Colonna, *Dissecting natural killer cell activation pathways through analysis of genetic mutations in human and mouse.* Immunol Rev, 2006. 214: p. 92-105.
33. Wortham, B. W., et al., *NKG2D mediates NK cell hyperresponsiveness and influenza-induced pathologies in a mouse model of chronic obstructive pulmonary disease.* J Immunol, 2012. 188(9): p. 4468-75.
34. Borchers, M. T., et al., *The NKG2D-activating receptor mediates pulmonary clearance of Pseudomonas aeruginosa.* Infect Immun, 2006. 74(5): p. 2578-86.
35. Borchers, M. T., et al., *Sustained CTL activation by murine pulmonary epithelial cells promotes the development of COPD-like disease.* J Clin Invest, 2009. 119(3): p. 636-49.
36. Lie, M. L., et al., *Lung T lymphocyte trafficking and activation during ischemic acute kidney injury.* J Immunol, 2012. 189(6): p. 2843-51.
37. Shen, X., et al., *CD4 T cells promote tissue inflammation via CD40 signaling without de novo activation in a murine model of liver ischemia/reperfusion injury.* Hepatology, 2009. 50(5): p. 1537-46.
38. Ichim, C. V., *Revisiting immunosurveillance and immunostimulation: Implications for cancer immunotherapy.* J Transl Med, 2005. 3(1): p. 8.
39. Fraschini, F., et al., *Some aspects of "deep lung" cellular immunity in chronic bronchitis before and after therapy with tiopronin.* Int J Clin Pharmacol Res, 1987. 7(2): p. 129-33.
40. Mattoli, S., et al., *The role of CD8+Th2 lymphocytes in the development of smoking-related lung damage.* Biochem Biophys Res Commun, 1997. 239(1): p. 146-9.
41. Cosio, M. G. and A. Guerassimov, *Chronic obstructive pulmonary disease. Inflammation of small airways and lung parenchyma.* Am J Respir Crit Care Med, 1999. 160(5 Pt 2): p. S21-5.
42. Stankiewicz, W., et al., *Cellular and cytokine immunoregulation in patients with chronic obstructive pulmonary disease and bronchial asthma.* Mediators Inflamm, 2002. 11(5): p. 307-12.
43. Agostini, C., L. Trentin, and F. Adami, *Chronic obstructive pulmonary disease (COPD): new insights on the events leading to pulmonary inflammation.* Sarcoidosis Vasc Diffuse Lung Dis, 2003. 20(1): p. 3-7.
44. Glader, P., K. von Wachenfeldt, and C. G. Lofdahl, *Systemic CD4+T-cell activation is correlated with FEV1 in smokers.* Respir Med, 2006. 100(6): p. 1088-93.
45. Di Stefano, A., et al., *STAT4 activation in smokers and patients with chronic obstructive pulmonary disease.* Eur Respir J, 2004. 24(1): p. 78-85.
46. Roos-Engstrand, E., et al., *Cytotoxic T cells expressing the co-stimulatory receptor NKG2 D are increased in cigarette smoking and COPD.* Respir Res, 2010. 11: p. 128.
47. Hou, J., et al., *Imbalance between subpopulations of regulatory T cells in COPD.* Thorax, 2013.
48. Wang, H., et al., *Imbalance of Th17/Treg cells in mice with chronic cigarette smoke exposure.* Int Immunopharmacol, 2012. 14(4): p. 504-12.
49. Eppert, B. L., et al., *Functional characterization of T cell populations in a mouse model of chronic obstructive pulmonary disease.* J Immunol, 2013. 190(3): p. 1331-40

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of treating or preventing lung disease or lung degeneration in an individual, comprising the step of administering an effective amount of fibroblasts to an individual with lung disease or lung degeneration or at risk for lung disease or lung degeneration, wherein the fibroblasts express one or more markers selected from the group consisting of CD31, CD73, and a combination thereof.

2. The method of claim 1, wherein the fibroblasts are activated by exposure to at least one toll like receptor agonist and/or by exposure to Activated Protein C.

3. The method of claim 2, wherein the toll like receptor is TLR-1, TLR-2, TLF-3, TLR-4, TLR-5, TLR-6, TLR-7, TLR-8, or TLR-9.

4. The method of claim 1, wherein the lung disease is chronic obstructive pulmonary disease, asthma, partial or complete lung collapse, lung infection, pulmonary edema, pulmonary embolus, bronchitis, emphysema, or a combination thereof.

5. The method of claim 1, wherein the individual is or was a smoker.

6. The method of claim 1, wherein the individual is provided an effective amount of another therapy for the lung disease.

7. The method of claim 6, wherein the other therapy comprises short- and long-acting beta2-agonists, anticholinergics, one or more corticosteroids, one or more phosphodiesterase-4 inhibitors, theophylline, supplemental oxygen therapy, and/or surgery.

\* \* \* \* \*

UNITED STATES PATENT AND TRADEMARK OFFICE
CERTIFICATE OF CORRECTION

| | | |
|---|---|---|
| PATENT NO. | : 11,975,030 B2 | Page 1 of 1 |
| APPLICATION NO. | : 16/822811 | |
| DATED | : May 7, 2024 | |
| INVENTOR(S) | : O'Heeron et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 605 days.

Signed and Sealed this
Eighth Day of October, 2024

Katherine Kelly Vidal
*Director of the United States Patent and Trademark Office*